United States Patent [19]
Matson et al.

[11] Patent Number: 5,981,185
[45] Date of Patent: Nov. 9, 1999

[54] OLIGONUCLEOTIDE REPEAT ARRAYS

[75] Inventors: Robert S. Matson, Orange; Peter J. Coassin, San Juan Capistrano; Jang B. Rampal, Yorba Linda, all of Calif.; Charles Thomas Caskey, Houston, Tex.

[73] Assignee: Beckman Coulter, Inc., Fullerton, Calif.

[21] Appl. No.: 08/863,639

[22] Filed: May 28, 1997

Related U.S. Application Data

[63] Continuation of application No. 08/239,475, May 5, 1994, abandoned.

[51] Int. Cl.⁶ .............. C12Q 1/68; C07H 21/02; C07H 21/00
[52] U.S. Cl. .............. 435/6; 435/395; 536/22.1; 536/25.32; 536/25.4; 536/25.5; 204/606
[58] Field of Search .............. 435/6, 395, 401; 204/182.8, 606; 536/22.1, 25.32, 25.4, 25.5

[56] References Cited

U.S. PATENT DOCUMENTS

| | | | |
|---|---|---|---|
| 5,021,335 | 6/1991 | Tecott et al. | 435/6 |
| 5,449,604 | 9/1995 | Schellenberg et al. | 435/6 |

FOREIGN PATENT DOCUMENTS

| | | | |
|---|---|---|---|
| WO89/10977 | 11/1989 | WIPO | C12Q 1/68 |
| WO92/10588 | 6/1992 | WIPO | C12Q 1/68 |
| WO93/17126 | 9/1993 | WIPO | C12Q 1/68 |

OTHER PUBLICATIONS

Armour, J.A.L. et al., *Human Molecular Genetics*, 1994, vol. 3, No. 4 599–605.
Karagyozov, L. et al., *Nucleic Acids Research*, 1993, vol. 21, No. 16 3911–3912.
Iizuka, M. et al., *GATA*, 1993, 10(1): 2–5.
Wehnert, M.S. et al., *Nucleic Acids Research*, 1994, vol. 22, No. 9 1701–1704.

*Primary Examiner*—Ardin H. Marschel
*Assistant Examiner*—Joyce Tung
*Attorney, Agent, or Firm*—William H. May; Margaret A. Kivinski; Sheldon & Mak

[57] ABSTRACT

A solid support based hybridization assay is provided which allows for the systematic and reproducible analysis of repeat and tandem repeat oligonucleotide sequences of DNA and RNA by hybridization to a reverse dot blot array comprising strings of such repeats complementary to those found in particular nucleic acid targets (e.g., analyte PCR product). An addressable library (i.e., an indexed set) of complementary repeats is synthesized on a suitable support. Preferably, the support comprises a low fluorescent background support, thereby facilitating the use of non-radioisotopic modes of detection (such as fluorescence or chemiluminescence); particularly suitable in this regard is an aminated polypropylene support or similar material. Preferred arrays permit screening of DNA and RNA samples for complete sets of particular types of nucleotide repeat sequences (e.g., all nucleotide doublet or triplet repeats).

2 Claims, 3 Drawing Sheets

Fig. 1

SEQUENCE LISTING (1) GENERAL INFORMATION:

(iii) NUMBER OF SEQUENCES: 95

(2) INFORMATION FOR SEQ ID NO:1:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:1:

CCCACGACGA CG                                          12

(2) INFORMATION FOR SEQ ID NO:2:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:2:

CCCGACGACG AC                                          12

(2) INFORMATION FOR SEQ ID NO:3:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:3:

ACGACGATCA TC                                          12

(2) INFORMATION FOR SEQ ID NO:4:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:4:

ACATACATAC AT                                          12

(2) INFORMATION FOR SEQ ID NO:5:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:5:

AAAAAAAAAA AAAAA                                                              15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:6:

AAAAACAACA ACAAC                                                              15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:7:

ACAAAAAAAA AAAAA                                                              15

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:8:

TTTAAAAAAA AAAAA                                                              15

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:9:

TTTTTTTTTT TTTTT                                                              15

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:10:

AAAAAAAAAA AAAAAAAAAA A                                                       21

(2) INFORMATION FOR SEQ ID NO:11:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Other nucleic acid (xi) SEQUENCE DESCRIPTION: SEQ ID NO:11:

CCCCCCCCCC CCCCCCCCCC C                                        21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:12:

GGGGGGGGGG GGGGGGGGGG G                                        21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:13:

TTTTTTTTTT TTTTTTTTTT T                                        21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:14:

AACAACAACA ACAACAACAA C                                        21

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:15:

ACAACAACAA CAACAACA                                            18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:16:

CAACAACAAC AACAACAA                                                         18

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:17:

TGCTGCTGCT GCTGCTGC                                                         18

(2) INFORMATION FOR SEQ ID NO:18:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:18:

TGCTGCTGCT GCTGTGTGTG TGTGTTATTA TTATTA                                     36

(2) INFORMATION FOR SEQ ID NO:19:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:19:

TGGTGGTGGT GGTGATGATG ATGA                                                  24

(2) INFORMATION FOR SEQ ID NO:20:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:20:

TCGTCGTCGT CGTCGTCG                                                         18

(2) INFORMATION FOR SEQ ID NO:21:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:21:

GGCGGCGGCG GCGGC                                                    15

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:22:

CGCGCGCGGA CGACGACGAC                                               20

(2) INFORMATION FOR SEQ ID NO:23:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:23:

TCATCATCAT CATAATAATA ATAATACTAC TACTAC                             36

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:24:

CCACCACCAC CACAACAACA ACAA                                          24

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:25:

TTCTTCTTCT TCTCTCTCTC TCTCTCCTCC TCCTCC                             36

(2) INFORMATION FOR SEQ ID NO:26:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:26:

GAAGAAGAAG AAGAGAGAGA GAGAGGAGGA GGAGGA                             36

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:27:

GCCGCCGCCG CCGCAGCAGC AGCA                                              24

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:28:

CAGCAGCAGC AGCAGCAGCA G                                                 21

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:29:

CTGCTGCTGC TGCTGCTGCT GCTGCTGCTG CTG                                    33

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:30:

CAGCAGCAGC AGCAGCAGCA GCAGCAGCAG                                        30

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:31:

GCAGCAGCAG CAGCAGCAGC AGCAGCGGCG GCGGCG                                 36

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:32:

ACACACACAC ACACACACAC                                            20

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:33:

AAGAAGAAGA AGAAGAAGAA G                                          21

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:34:

AATAATAATA ATAATAATAA T                                          21

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:35:

ACAACAACAA CAACAACAAC A                                          21

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:36:

ACCACCACCA CCACCACCAC C                                          21

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:37:

ACGACGACGA CGACGACGAC G                                          21

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:38:

ACTACTACTA CTACTACTAC T                                          21

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:39:

AGAAGAAGAA GAAGAAGAAG A                                          21

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:40:

AGCAGCAGCA GCAGCAGCAG C                                          21

(2) INFORMATION FOR SEQ ID NO:41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:41:

AGGAGGAGGA GGAGGAGGAG G                                          21

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:42:

AGTAGTAGTA GTAGTAGTAG T                                          21

(2) INFORMATION FOR SEQ ID NO:43:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:43:

ATAATAATAA TAATAATAAT A                                              21

(2) INFORMATION FOR SEQ ID NO:44:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: Other nucleic acid (xi) SEQUENCE DESCRIPTION: SEQ ID NO:44:

ATCATCATCA TCATCATCAT C                                              21

(2) INFORMATION FOR SEQ ID NO:45:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: Other nucleic acid (xi) SEQUENCE DESCRIPTION: SEQ ID NO:45:

ATGATGATGA TGATGATGAT G                                              21

(2) INFORMATION FOR SEQ ID NO:46:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: Other nucleic acid (xi) SEQUENCE DESCRIPTION: SEQ ID NO:46:

ATTATTATTA TTATTATTAT T                                              21

(2) INFORMATION FOR SEQ ID NO:47:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: Other nucleic acid (xi) SEQUENCE DESCRIPTION: SEQ ID NO:47:

CAACAACAAC AACAACAACA A                                              21

(2) INFORMATION FOR SEQ ID NO:48:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: Other nucleic acid (xi) SEQUENCE DESCRIPTION: SEQ ID NO:48:

CACCACCACC ACCACCACCA C                                              21

(2) INFORMATION FOR SEQ ID NO:49:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:49:

CATCATCATC ATCATCATCA T                                              21

(2) INFORMATION FOR SEQ ID NO:50:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:50:

CCACCACCAC CACCACCACC A                                              21

(2) INFORMATION FOR SEQ ID NO:51:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:51:

CGCGCGCGCG CGCGCGCGCG                                                20

(2) INFORMATION FOR SEQ ID NO:52:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:52:

CCGCCGCCGC CGCCGCCGCC G                                              21

(2) INFORMATION FOR SEQ ID NO:53:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other nucleic acid (xi) SEQUENCE DESCRIPTION: SEQ ID NO:53:

```
CCTCCTCCTC CTCCTCCTCC T                                                      21
```

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:54:

```
CGACGACGAC GACGACGACG A                                                      21
```

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:55:

```
CGCCGCCGCC GCCGCCGCCG C                                                      21
```

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:56:

```
CGGCGGCGGC GGCGGCGGCG G                                                      21
```

(2) INFORMATION FOR SEQ ID NO:57:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:57:

```
CGTCGTCGTC GTCGTCGTCG T                                                      21
```

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:58:

```
CTACTACTAC TACTACTACT A                                                      21
```

(2) INFORMATION FOR SEQ ID NO:59:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Other nucleic acid (xi) SEQUENCE DESCRIPTION: SEQ ID NO:59:

CTCCTCCTCC TCCTCCTCCT C                                          21

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:60:

CTGCTGCTGC TGCTGCTGCT G                                          21

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:61:

CTTCTTCTTC TTCTTCTTCT T                                          21

(2) INFORMATION FOR SEQ ID NO:62:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:62:

GAAGAAGAAG AAGAAGAAGA A                                          21

(2) INFORMATION FOR SEQ ID NO:63:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:63:

GACGACGACG ACGACGACGA C                                          21

(2) INFORMATION FOR SEQ ID NO:64:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:64:

GAGGAGGAGG AGGAGGAGGA G                                               21

(2) INFORMATION FOR SEQ ID NO:65:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:65:

GATGATGATG ATGATGATGA T                                               21

(2) INFORMATION FOR SEQ ID NO:66:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:66:

GCAGCAGCAG CAGCAGCAGC A                                               21

(2) INFORMATION FOR SEQ ID NO:67:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:67:

GCCGCCGCCG CCGCCGCCGC C                                               21

(2) INFORMATION FOR SEQ ID NO:68:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:68:

GCGGCGGCGG CGGCGGCGGC G                                               21

(2) INFORMATION FOR SEQ ID NO:69:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: Other nucleic acid (xi) SEQUENCE DESCRIPTION: SEQ ID NO:69:

```
GCTGCTGCTG CTGCTGCTGC T                                                21

(2) INFORMATION FOR SEQ ID NO:70:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:70:

GGAGGAGGAG GAGGAGGAGG A                                                21

(2) INFORMATION FOR SEQ ID NO:71:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:71:

GGCGGCGGCG GCGGCGGCGG C                                                21

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:72:

AGAGAGAGAG AGAGAGAGAG                                                  20

(2) INFORMATION FOR SEQ ID NO:73:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:73:

GGTGGTGGTG GTGGTGGTGG T                                                21

(2) INFORMATION FOR SEQ ID NO:74:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:74:

GTAGTAGTAG TAGTAGTAGT A                                                21

(2) INFORMATION FOR SEQ ID NO:75:
```

-continued (i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:75:

GTCGTCGTCG TCGTCGTCGT C                                              21

(2) INFORMATION FOR SEQ ID NO:76:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:76:

GTGGTGGTGG TGGTGGTGGT G                                              21

(2) INFORMATION FOR SEQ ID NO:77:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:77:

GTTGTTGTTG TTGTTGTTGT T                                              21

(2) INFORMATION FOR SEQ ID NO:78:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:78:

TAATAATAAT AATAATAATA A                                              21

(2) INFORMATION FOR SEQ ID NO:79:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:79:

TACTACTACT ACTACTACTA C                                              21

(2) INFORMATION FOR SEQ ID NO:80:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Other nucleic acid (xi) SEQUENCE DESCRIPTION: SEQ ID NO:80:

TAGTAGTAGT AGTAGTAGTA G                                    21

(2) INFORMATION FOR SEQ ID NO:81:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:81:

TATTATTATT ATTATTATTA T                                    21

(2) INFORMATION FOR SEQ ID NO:82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:82:

TCATCATCAT CATCATCATC A                                    21

(2) INFORMATION FOR SEQ ID NO:83:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:83:

TCCTCCTCCT CCTCCTCCTC C                                    21

(2) INFORMATION FOR SEQ ID NO:84:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:84:

TCGTCGTCGT CGTCGTCGTC G                                    21

(2) INFORMATION FOR SEQ ID NO:85:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:85:

```
TCTTCTTCTT CTTCTTCTTC T                                              21

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:86:

TGATGATGAT GATGATGATG A                                              21

(2) INFORMATION FOR SEQ ID NO:87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:87:

TGCTGCTGCT GCTGCTGCTG C                                              21

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:88:

TGGTGGTGGT GGTGGTGGTG G                                              21

(2) INFORMATION FOR SEQ ID NO:89:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:89:

TGTTGTTGTT GTTGTTGTTG T                                              21

(2) INFORMATION FOR SEQ ID NO:90:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:90:

TTATTATTAT TATTATTATT A                                              21

(2) INFORMATION FOR SEQ ID NO:91:
```

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: Other nucleic acid (xi) SEQUENCE DESCRIPTION: SEQ ID NO:91:

TTCTTCTTCT TCTTCTTCTT C                                              21

(2) INFORMATION FOR SEQ ID NO:92:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:92:

TTGTTGTTGT TGTTGTTGTT G                                              21

(2) INFORMATION FOR SEQ ID NO:93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:93:

CTCTCTCTCT CTCTCTCTCT                                                20

(2) INFORMATION FOR SEQ ID NO:94:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:94:

GCAGCAGCAG CAGCAGCAGC AGCA                                           24

(2) INFORMATION FOR SEQ ID NO:95:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO:95:

GCGGCGGCGG CG                                                        12

OLIGONUCLEOTIDE REPEAT ARRAYS

This application is a continuation of application Ser. No. 08/239,475 filed on May 5, 1994, now abandoned.

BACKGROUND OF THE INVENTION

The present invention relates generally to the fields of biochemistry and medicine. In particular, the invention is directed to materials and methods useful in the diagnosis of genetic mutations of clinical relevance.

Short tandem repeats (STR) have been identified in a number of genes. It has been proposed that particular unstable triplet repeat oligonucleotides are correlated with a number of genetic diseases in humans, including Kennedy's disease [La Spada, A. et al., *Nature,* 352, 77–79 (1991)], fragile-X syndrome [Verkerk, A. J. M. H. et al., *Cell* 65, 905–914 (1991)], myotonic dystrophy [Fu, Y. H. et al, *Science* 255, 1256–1258 (1992)], Huntington disease [The Huntington's Disease Collaborative Research Group, *Cell* 72, 971–983 (1993)] and spinocerebellar ataxia type 1 [Orr, H. T. et al., *Nature Genet.* 4, 221–226 (1993)]. Similarly, doublet repeats have also been reported to be associated with particular disease states; for example, correlations have been proposed with cystic fibrosis [Chu, C.-S. et al., *Nature Genetics* 3, 151–156 (1993)] and colorectal cancer [Thibodeau, S. N. et al., *Science* 260, 816–819 (1993)]. Higher-order repeats, such as tetramers [see, e.g., Gen, M. W. et al., *Genomics* 17, 770–772 (1993)], have also been identified.

One gene which has been subject of intense scrutiny is the Huntington's disease gene. The trinucleotide hybridization approach was recently utilized to map out tandem repeats across a section of the gene. In this section, 51 triplet repeats spanning a 1.86 Mbp DNA segment were identified by Southern transfer of restriction enzyme digests of a specific cosmid and probing with $^{32}$P-labelled oligonucleotide probes [Hummerich, et al., "Distribution of trinucleotide repeat sequences across a 2 Mbp region containing the Huntington's disease gene," *Human Molecular Genetics* 3, 73 (1994)].

DNA polymorphisms which arise from allelic differences in the number of repeats have been identified by such terminology as short tandem repeats (STR), variable number of tandem repeats (VNTR), minisatellites (tandem repeats of a short sequence, originally defined as 9–60 bp) and microsatellites (originally defined as 1–5 bp) [McBride, L. J. & O'Neill, M. D., *American Laboratory,* pp. 52–54 (November 1991)]; minisatellites and microsatellites would be considered subclasses of the VNTR. It is estimated that there are up to 500,000 microsatellite repeats distributed throughout the human genome, at an average spacing of 7000 bp. Therefore, it is apparent that most genes will contain VNTR regions and that these regions can be used as genetic markers. For example, VNTRs are currently being used as markers in studies concerned with the inheritance of certain mutations leading to various forms of cancer. Recently, it has been discovered that certain triplet repeat expansions are associated with a predisposition towards certain diseases; a large expansion is typically associated with the onset of the disease. For example, the (CGG) triplet repeat region associated with Fragile X occurs at a frequency of 10–50 repeat units in the normal population, while in those afflicted with the disease the expansion is between 200–2000 repeats.

As it becomes possible to determine whether a particular genotype comprises an unstable repeat and/or is associated with a particular disease state, there is a considerable incentive to develop useful methods to characterize STRs. The heretofore available methods for initial scanning for STRs have generally required time-consuming sequential oligonucleotide hybridizations to filter-bound target DNAs to identify specific STRs [see, e.g., Litt, M. and Luty, J. A., *Am. J. Hum. Genet.* 44, 397–401 (1989); Weber, J. L. and May, P. E., *Am. J. Hum. Genet.* 44, 388–396 (1989); Fu et al., supra]. In particular, the analysis of oligonucleotide repeats is typically carried out at the present time by Southern blotting of restriction fragments followed by hybridization analysis using a specified repetitive sequence probe. Alternatively, it is possible to probe dot blots of the target DNA [Iizuka, et al., *GATA* 10:2–5 (1993)].

Both of these heretofore-known techniques are time-consuming and tedious for large sample populations. Moreover, multiple probings may be required to identify which repeat might be present. Further, it is often difficult to reproducibly spot or transfer equivalent amounts of DNA to these supports; thus, conventional dot blots and transfers show variation in signal intensity from batch to batch. In addition, any regions of DNA that might become cross-linked to the support (e.g., through UV light) would be inaccessible to probes.

It would be highly useful for clinical investigators to be able to screen large sample populations of patients DNAs in an effective manner. As additional STRs are identified and associated with particular conditions, the need for simple and effective screening methods becomes greater.

PCT published application No. WO 89/10977 describes methods and apparatus for analyzing polynucleotide sequences in which an array of the whole or a chosen part of a complete set of oligonucleotides are bound to a solid support. The different oligonucleotides occupy separate cells of the array and are capable of taking part in hybridization reactions. For studying differences between polynucleotide sequences, the array may comprise the whole or a chosen part of a complete set of oligonucleotides comprising the polynucleotide sequences. While it is suggested that a small array may be useful for many applications, such as the analysis of a gene for mutations, there is no teaching or suggestion of a specific array or method for using same which would permit the rapid and accurate screening of a wide range of biological materials for tandem repeats. Moreover, the arrays described in WO 89/10977 are designed specifically for use in sequencing by hybridization; the presence of long tandem nucleotide repeats can present a significant problem in attempts to sequence a sample using the methods described in WO 89/10977.

It is an object of the present invention to provide methods and apparatus for rapid and accurate identification of nucleotide tandem repeats in DNA and RNA sequences from a wide variety of sources.

SUMMARY OF THE INVENTION

In accordance with the present invention, a solid support based hybridization assay is provided which allows for the systematic and reproducible analysis of repeat and tandem repeat oligonucleotide sequences of DNA and RNA by hybridization to a reverse dot blot array comprising strings of such repeats complementary to those found in particular nucleic acid targets (e.g., analyte PCR product). An addressable library (i.e., an indexed set) of complementary repeats is synthesized on a suitable support. Preferably, the support comprises a low fluorescent background support, thereby facilitating the use of non-radioisotopic modes of detection (such as fluorescence or chemiluminescence); particularly suitable in this regard is an aminated polypropylene support or similar material. Pursuant to a preferred embodiment of the invention, arrays are provided which permit screening of DNA and RNA samples for complete sets of particular types of nucleotide repeat sequences (e.g., all nucleotide doublet or triplet repeats).

BRIEF DESCRIPTION OF THE DRAWINGS

The invention may be better understood with reference to the accompanying drawings, in which:

FIG. 1 illustrates a pattern for synthesis of leader sequences and tandem repeat patterns;

FIGS. 2(A)–2(C) illustrate hybridization of arrayed dinucleotide and trinucleotide oligonucleotide repeats using $^{32}P$ labelled DNA of cosmid 22.3 as a probe, in which FIG. 2(A) represents hybridization stringency at 40° C., FIG. 2(B), hybridization stringency at 50° C., and FIG. 2(C), hybridization stringency at 60° C.

DETAILED DESCRIPTION OF THE INVENTION

Figure 2A:
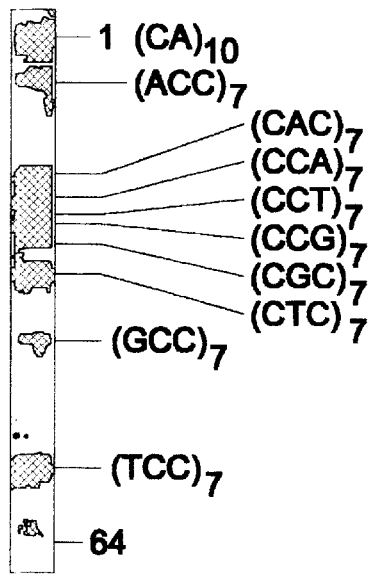

In accordance with the present invention, defined repeat and tandem repeat arrays for use in screening nucleic acid targets for the presence of genetic markers generally known as variable number [of] tandem repeats (VNTRs) are synthesized on a suitable support. After hybridization of the target materials with the array, the identity of any tandem repeat sequence(s) in the target materials may be readily ascertained by observing the location(s) at which binding occurs. Pursuant to the present invention, probes are reproducibly synthesized on the surface, freely accessible to target DNA. Moreover, all hybridizations can be rapidly identified under a limited number of stringency conditions.

The arrays of the present invention comprise a predetermined set of oligonucleotides attached to the surface of the solid support. One particularly useful class of tandem repeats for arrays in accordance with the present invention comprises the complete class of 60 tandem triplet repeats (i.e., all possible triplet combinations minus the four homopolymer combinations). Another useful class of tandem repeats is the complete class of 6 tandem doublet repeats (i.e., the 10 possible doublet combinations of the nucleic acids A, C, G and T minus the four homopolymer combinations). Of course, those skilled in the art would readily appreciate that a wide range of different combinations of repeat elements could also be employed in accordance with the present invention. For example, repeats of a higher order (i.e., repeats of four or more nucleotides) may be useful in some instances. In addition, particular subclasses of any complete class of all possible tandem repeats of a given size may be suitable for carrying out particular types of screenings. For purposes of the present invention, all predetermined sets of tandem repeats are contemplated as within the scope of the present invention.

Figure 1:
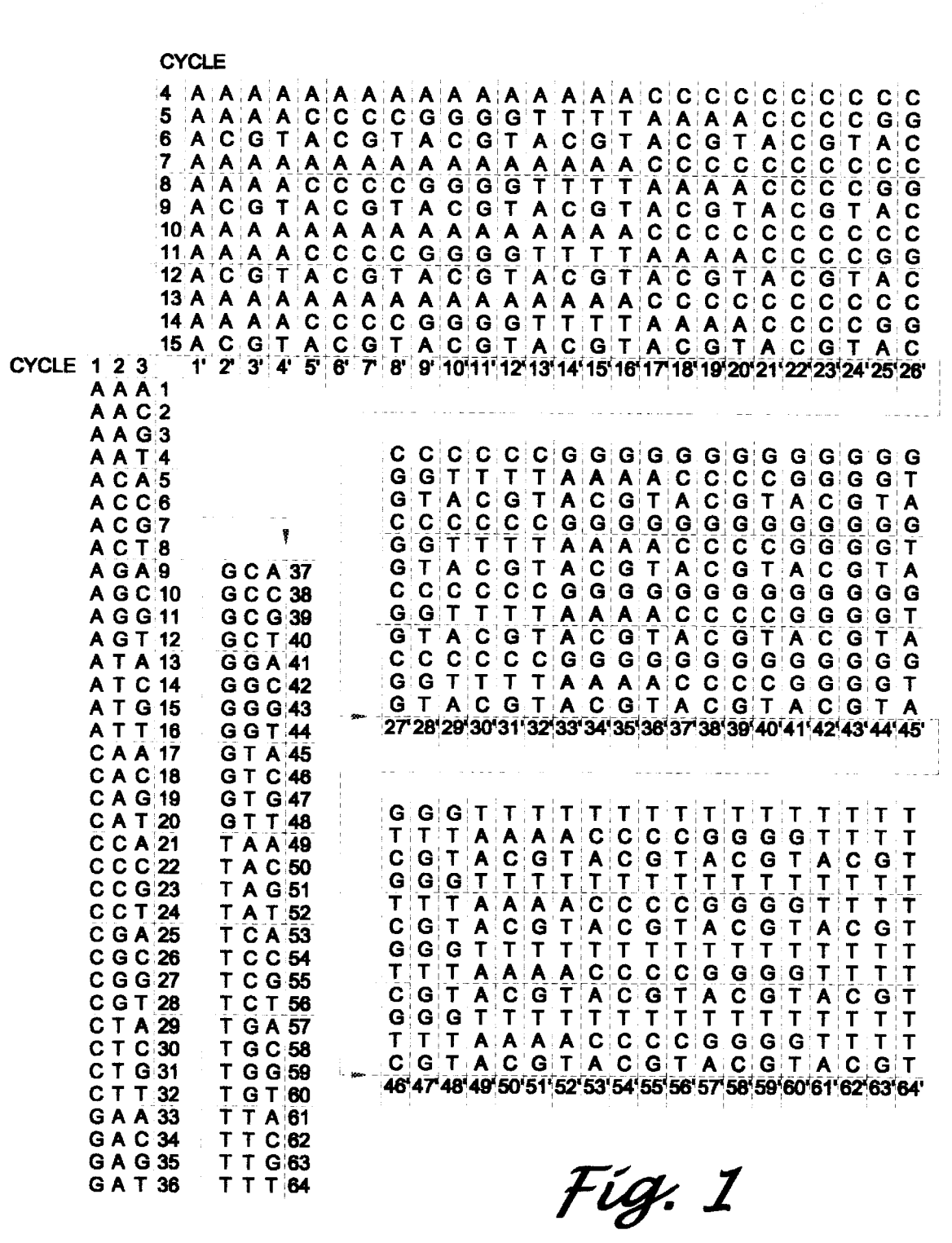

The sequences forming the array may be directly linked to the support. In other embodiments of the arrays of the present invention, the repeat units may be attached to the support by non-repetitive sequences of oligonucleotides or other molecules serving as spacers or linkers to the solid support. In preferred examples of this embodiment, specific leader sequences are encoded on either side of the tandem repeat region in an array format. Depending upon the relative position of the leader sequence a PCR or sequencing primer may be designed. Such primers may then be used to aid in the characterization of the length of the tandem repeat and/or the specific flanking sequences, respectively. In general, a triplet tandem repeat sequence of sufficient length effectively defines two additional tandem repeat sequences; for example, a 21 mer complementary to $(ACG)_n$ also hybridizes to $(GAC)_n$ and $(CGA)_n$. By systematically including a degenerate set of leader sequences while reducing the size of the tandem repeat region, hybridization stringency is increased to allow for identification of the combination of leader plus the tandem repeat; in the example, selectivity of CCC ACG ACG ACG [SEQ ID NO:1] would be observed over, e.g., CCC GAC GAC GAC [SEQ ID NO:2]. FIG. 1 illustrates a set of instructions for synthesis of suitable leader sequences for triplet tandem repeats. Such leader arrays are particularly advantageous for the purpose of identifying leader sequences for use as PCR primers to tandem repeat regions.

The method of the present invention is generally applicable to a wide range of tandem repeat patterns, including higher order tandem repeats. As by definition a tandem repeat consists of at least 2 units of a given oligomer (for example, a dimer or 2 mer), then a $(2 \text{ mer})_n$ wherein n=2, 3, 4 . . . would represent a dinucleotide repeat forming a 4 mer, 6 mer, 8 mer, etc. (e.g., ACAC, ACACAC, ACACACAC, etc.). Similarly, a triplet repeat would be defined as a $(3 \text{ mer})_n$ and a tetramer repeat as $(4 \text{ mer})_n$, wherein n represents the number of repeats present. Contemplated as within the scope of the present invention are all tandem repeats of the general formula $(Nmer)_n$ wherein N is an integer greater than 1 representing the number of nucleotides in the repeat pattern and n is an integer representing the number of times the pattern is repeated; in general, the product of N and n is in the range of 4 to about 100, and preferably 6 to about 60.

Higher order tandem repeat combinations representing combinations of two or more individual tandem repeats are also contemplated as within the scope of the present invention; for example, such higher order tandem repeat combinations may include two dimer patterns, a dimer and a triplet, two triplets, etc. In general terms, such repeat combinations may be described as $$(Nmer)_n(Mmer)_m$$

in which N and M are independently selected integers greater than 1 and represent the number of nucleotides in the respective repeat pattern and n and m are independently selected integers and represent the number of times the respective pattern is repeated. In the case of three tandem patterns, the structure may be represented as $$(Nmer)_n(Mmer)_m(Pmer)_p$$

in which P is defined in the same manner as N and M, and p in the same manner as n and m. Moreover, these higher order tandem repeat combinations may also be found in a repeat pattern; such a complex higher order tandem repeat combination may be described as $$[(Nmer)_n(Mmer)_m]_x$$

or $$[(Nmer)_n(Mmer)_m(Pmer)_p]_x$$

in which N, M, P, n, m and p are as previously defined and x is an integer which represents the number of times the $[(Nmer)_n(Mmer)_m]$ or $[(Nmer)_n(Mmer)_m(Pmer)_p]$ pattern is repeated. Contemplated as within the scope of the present invention are those combinations wherein x(Nn+Mm) or x(Nn+Mm+Pp) is in the range of 4 to about 100, preferably in the range of 6 to about 60. In the simplest case comprising two repeat patterns and wherein x is 1, N and M are both 2 and n and m are both 1; 1×2+1×2=4. Table 1 illustrates the construction of higher order repeats in which n and m are both 2.

TABLE 1

| Tandem Repeat | $(2 \text{ mer})_n$ | $(3 \text{ mer})_n$ | $(4 \text{ mer})_n$ | $(5 \text{ mer})_n$ | $(6 \text{ mer})_n$ | $(7 \text{ mer})_n$ |
| --- | --- | --- | --- | --- | --- | --- |
| $(2 \text{ mer})_m$ | 8 mer | 10 mer | 12 mer | 14 mer | 16 mer | 18 mer |
| $(3 \text{ mer})_m$ | 10 mer | 12 mer | 14 mer | 16 mer | 18 mer | 20 mer |
| $(4 \text{ mer})_m$ | 12 mer | 14 mer | 16 mer | 18 mer | 20 mer | 22 mer |
| $(5 \text{ mer})_m$ | 14 mer | 16 mer | 18 mer | 20 mer | 22 mer | 24 mer |
| $(6 \text{ mer})_m$ | 16 mer | 18 mer | 20 mer | 22 mer | 24 mer | 26 mer |
| $(7 \text{ mer})_m$ | 18 mer | 20 mer | 22 mer | 24 mer | 26 mer | 28 mer |

Thus, for example, the 8 mer comprising a $(2 \text{ mer})_n=(AC)_2$ and a $(2 \text{ mer})_m=(AT)_2$ would have the formula ACACATAT; similarly, the 12 mer comprising a $(3 \text{ mer})_n=(ACG)_2$ and a $(3 \text{ mer})_m=(ATC)_2$ would have the formula ACGACGAT-CATC [SEQ ID NO:3]. A complex higher order repeat $[(AC)_n(AT)_m]_x$ in which n and m are 1 and x is 2 would have the formula ACATACAT; where x is 3, the formula would be ACATACATACAT [SEQ ID NO:4]. Those skilled in the art would readily appreciate the variety of simple and higher-order tandem repeat patterns falling within the scope of the present invention.

The methods and apparatus in accordance with the present invention take advantage of the fact that under appropriate conditions oligonucleotides form base paired duplexes with oligonucleotides which have a complementary base sequence. The stability of the duplex is dependent on a number of factors, including the length of the oligonucleotides, the base composition, and the composition of the solution in which hybridization is effected. The effects of base composition on duplex stability may be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated Tm's of the type of duplexes expected to be formed between the target material(s) and the oligonucleotides bound to the array, the rate of formation of mismatched duplexes may be substantially reduced.

The number of repeats in the tandem sequences attached to the array may vary over a broad range from the minimum of two necessary to constitute a repeat to a maximum on the order of about 50. Of course, the optimum range for the number of tandem repeats in any given instance is dependent upon a number of factors, including in particular the composition and the length of the repeat. In general, the Tm of the complex formed between a given sequence in the target material and the complementary sequence in the array increases as the length of the sequences increase; however, only minor increases in Tm are observed once the sequences have reached a length of about 50–60 bases. The sequences on the array contain at least four bases (the minimum for a repeat of a doublet pattern). It is generally preferred that the sequences on the array comprise at least about 6 bases, more preferably at least about 10 bases, and most preferably on the order of about 15 to about 60 bases. As previously noted, there is little practical advantage in using sequences substantially longer than about 60 bases; nonetheless, extended sequences of up to about 100 bases in length (corresponding to, e.g., 50 repeats of a doublet sequence) and longer are also contemplated as within the scope of the present invention.

In addition, in accordance with preferred embodiments of the invention the length of each sequence employed in the array may be selected to as to optimize binding of target materials to the array. For any given tandem repeat sequence, an optimum length for use with any particular target material under specified screening conditions may be determined empirically. Thus, the length for each individual element of the set of tandem repeats comprising the array may be optimized for the screening of particular target materials under specific conditions (e.g., at a given temperature).

A wide variety of array formats may be employed in accordance with the present invention. One particularly useful format is a linear array of oligonucleotide bands, generally referred to in the art as a dipstick. Another suitable format comprises a two-dimensional pattern of discrete cells (e.g., 4096 squares in a 64 by 64 array). Of course, as would be readily appreciated by those skilled in the art, other array formats (e.g., circular) would be equally suitable for use in accordance with the present invention. While arrays may be prepared on a variety of materials including glass plates, it is presently preferred to use an organic polymer medium. As used herein, the term "organic polymer" is intended to mean a support material which is most preferably chemically inert under conditions appropriate for biopolymer synthesis and which comprises a backbone comprising various elemental substituents including, but not limited to, hydrogen, carbon, oxygen, fluorine, chlorine, bromine, sulfur and nitrogen. Representative polymers include, but are not limited to, the following: polypropylene, polyethylene, polybutylene, polyisobutylene, polybutadiene, polyisoprene, polyvinylpyrrolidone, polytetrafluoroethylene, polyvinylidene difluoride, polyfluoroethylene-propylene, polyethylene-vinyl alcohol, polymethylpentene, polychlorotrifluoroethylene, polysulfones, and blends and copolymers thereof. As used herein, the term "medium" is intended to mean the physical structural shape of the polymer. Thus, medium can be generally defined as polymer films (i.e., polymers having a substantially non-porous surface); polymer membranes (i.e., polymers having a porous surface); polymer filaments (e.g., mesh and fabrics); polymer beads; polymer foams; polymer frits; and polymer threads. Preferably, the polymer medium is a thread, membrane or film; most preferably, the polymer medium is a film. An exemplary organic polymer medium is a polypropylene sheet having a thickness on the order of about 1 mil (0.001 inch), although the thickness of the film is not critical and may be varied over a fairly broad range. Particularly preferred for preparation of arrays at this time are biaxially oriented polypropylene (BOPP) films; in addition to their durability, BOPP films exhibit a low background fluorescence.

The array formats of the present invention may be included in a variety of different types of device. As used herein, the term "device" is intended to mean any device to which the solid support can be affixed, such as microtiter plates, test tubes, inorganic sheets, dipsticks, etc. For example, when the solid support is a polypropylene thread, one or more polypropylene threads can be affixed to a plastic dipstick-type device; polypropylene membranes can be affixed to glass slides. The particular device is, in and of itself, unimportant. All that is necessary is that the solid support can be affixed thereto without affecting the functional behavior of the solid support or any biopolymer adsorbed thereon, and that the device is stable to any materials into which the device is introduced (e.g., clinical samples, etc.).

The arrays of the present invention may be prepared by a variety of approaches which are known to those working in the field. Pursuant to one type of approach, the complete sequences are synthesized separately and then attached to a solid support. However, it is presently considered particularly advantageous to synthesize the sequences directly onto the support to provide the desired array. Suitable methods for covalently coupling oligonucleotides to a solid support and for directly synthesizing the oligonucleotides onto the support would be readily apparent to those working in the field; a summary of suitable methods may be found in, e.g., Matson, R. S. et al., *Analytical Biochem.* 217, 306–310 (1994), hereby incorporated by reference. Advantageously, the oligonucleotides are synthesized onto the support using conventional chemical techniques as heretofore employed for preparing oligonucleotides on solid supports comprising, e.g., controlled pore size glass (CPG), as described for example in PCT applications WO 85/01051 and WO 89/10977, or polypropylene, as described in copending U.S. patent application Ser. No. 07/091,100, which has been assigned to the assignee of the present application and is herein incorporated by reference. Pursuant to one preferred approach, a polypropylene support (for example, a biaxially-oriented polypropylene) is first surface aminated by exposure to an ammonia plasma generated by radiofrequency plasma discharge. The reaction of a phosphoramidite-activated nucleotide with the aminated membrane followed by oxidation with, e.g., iodine provides a base stable amidate bond to the support.

As described in U.S. patent application Ser. No. 08/144,954 filed Oct. 28, 1993, which has been commonly assigned to the assignee of the present invention and is incorporated by reference herein, a suitable array may advantageously be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first (1°) direction, the substrate may then be rotated by 90° to permit synthesis to proceed within a second (2°) set of rows that are now perpendicular to the first set. This process creates a multiple-channel array whose intersection generates a plurality of discrete cells. Table 2 describes an exemplary vertical array of 64 oligonucleotides consisting of 60 triplet tandem repeat sequences (21 mers) and dinucleotide tandem repeat sequences (20 mers).

For the example of the preferred array comprising specific leader sequences as described in FIG. 1 (and as more fully described in the above-noted U.S. patent application Ser. No. 08/144,954), all of the degenerate triplet repeats (n=64, including homopolymers) are synthesized in a first direction (1° synthesis) in the 64 channels in Cycles 1–3 as 3' Leader Sequences (LLL). For example, lane 1 is AAA, lane 2 AAC, lane 5 ACA and lane 64 TTT. Then, the film is rotated 90° to perform synthesis in the second direction (20 synthesis or cross-synthesis) in Cycles 4–15. All 64 triplet tandem repeat sequences of $(NNN)_4$ are then produced. The 2-dimensional array created thereby is the product of a bidirectional synthesis and comprises 4096 discrete cells containing 15 mer oligonucleotide products $(LLL)(NNN)_4$, in which the Leader Sequence is placed at the 3'-end of each completed oligonucleotide. Thus, the following sequences would be found at the indicated cell positions:

| Cell 1,1'   | $(AAA)(AAA)_4$ | [SEQ ID NO:5] |
|---|---|---|
| Cell 1,2'   | $(AAA)(AAC)_4$ | [SEQ ID NO:6] |
| Cell 5,1'   | $(ACA)(AAA)_4$ | [SEQ ID NO:7] |
| Cell 64,1'  | $(TTT)(AAA)_4$ | [SEQ ID NO:8] |
| Cell 64,64' | $(TTT)(TTT)_4$ | [SEQ ID NO:9] |

This type of array comprising leader sequences (at either the 5' or 3' end) is particularly preferred in accordance with the present invention.

In order to accommodate a suitably large array, the pixel size should be as small as possible. Cells having a width on the order of about 10 μm to about 1 mm would be particularly suitable. In one preferred embodiment of the invention, arrays with a pixel width of about 500 μm are prepared on biaxially-oriented polypropylene.

Pursuant to the present invention, there are also provided methods for screening DNA and RNA samples comprising labelling the samples to form labelled material, applying the labelled material under suitable hybridization conditions to an array as described herein, and observing the location of the label on the surface associated with particular members of the set of oligonucleotides. Identification of the cell(s) in which binding occurs permits a rapid and accurate identification of any nucleotide repeats present in the sample from which the probes are derived.

In a hybridization reaction in accordance with the present invention, the array is explored by the labelled target material in essentially the same manner as a labelled probe is employed to screen, e.g., a DNA library containing a gene complementary to the probe. The target material may suitably comprise labelled sequences amplified from genomic DNA by the polymerase chain reaction (PCR), a mRNA population, or a partial or complete set of oligonucleotides from one or more chromosomes or an entire genome. To prepare the target material, the sample may be degraded to form fragments; where appropriate, the degraded material may then be sorted (for example, by electrophoresis on a sequencing gel) to provide a set of oligomers having a specific length.

The target material is then labelled to facilitate detection of duplex formation Suitably, conventional methods for end-labelling of oligomers are employed. Both radioactive and fluorescent labelling methods would be suitable for use in accordance with the present invention. Commonly-employed techniques routinely permit the introduction of label into a significant fraction of the target materials. Using conventional methods for labelling oligomers with $^{32}P$, for example, the radioactive yield of any individual oligomer even from a total human genome could be more than $10^4$ dpm/mg of total DNA. For detection, only a small fraction of the labelled material would be necessary for hybridization to a pixel of a size within the preferred range specified herein. Hybridization conditions for a given combination of array and target material can routinely be optimized in an empirical manner to be close to the Tm of the expected duplexes, thereby maximizing the discriminating power of the method. Autoradiography (in particular, with 32P) may cause image degradation which may be a limiting factor determining resolution; the limit for silver halide films is about 25 μm. Accordingly, the use of fluorescent probes (in particular, in conjunction with an array prepared on a low-fluorescence solid support) is presently preferred. In view of the low background fluorescence of the preferred biaxially-oriented polypropylene substrate, fluorescence-based labelling techniques may advantageously be employed with arrays on such a substrate. With either type of labeled target material, the substantial excess in bound oligonucleotides of the array makes it possible to operate at conditions close to equilibrium with most types of target materials contemplated herein.

As would be readily understood by those skilled in the art, the chosen conditions of hybridization must be such as to permit discrimination between exactly matched and mismatched oligonucleotides. Hybridization conditions may be initially chosen to correspond to those known to be suitable in standard procedures for hybridization to filters and then optimized for use with the arrays of the present invention; moreover, conditions suitable for hybridization of one type of target material would appropriately be adjusted for use with other target materials for the same array. In particular, it is appropriate to control temperature closely (preferably, to better than about ±1° C.) to substantially eliminate formation of duplexes between sequences other than identical sequences. Particularly when the length of the oligonucleotide in the target materials is small, it is necessary to be able to distinguish between slight differences in the rate and/or extent of hybridization.

A variety of heretofore known hybridization solvents may suitably be employed, the choice of solvent for particular hybridizations being dependent on a number of considerations. For example, G:C base pairs are more stable than A:T base pairs in 1 M NaCl; thus, the Tm of double-stranded oligonucleotides with a high G+C content will be higher than corresponding oligonucleotides with a high A+T content. These effects are of course particularly pronounced in sequences comprising tandem nucleotide repeats. In order to compensate for this discrepancy, a variety of approaches may be employed. For example, the amount of oligonucleotide applied to the surface of the support may be varied in dependence on the nucleotide composition of the bound oligomer. Further, computer means employed to analyze data from hybridization experiments may be programmed to make compensations for variations in nucleotide compositions. Another expedient (which may be employed instead of or in addition to those already mentioned) is the use of a chaotropic hybridization solvent, such as a ternary or quaternary amine. In this regard, tetramethylammonium chloride (TMACl) at concentrations in the range of about 2 M to about 5.5 M is particularly suitable; at TMACl concentrations around 3.5 to 4 M, the Tm dependence on nucleotide composition is substantially reduced. In addition, the choice of hybridization salt has a major effect on overall hybridization yield; for example, TMACl at concentrations up to 5 M can increase the overall hybridization yield by a factor of up to 30 or more (depending to some extent on the nucleotide composition) compared to 1 M NaCl. Finally, as previously noted, the length of the oligonucleotides attached to the array may be varied so as to optimize hybridization under the particular conditions employed. As previously noted, it would be a routine matter for those working in the field to optimize hybridization conditions for any given combination of target materials and array.

Hybridization is typically carried out with a very large excess of the bound oligonucleotides over what is found in the target. In preferred embodiments of the invention, it is possible in some cases to distinguish between hybridization involving single and multiple occurrences of the target sequence, as yield is proportional to concentration at all stages in the reaction.

In accordance with another embodiment of the present invention, an array as described herein may be employed to selectively isolate and size variable number of tandem repeats (VNTRs). This is accomplished by preparing a sample comprising VNTRs in a manner known per se [see, e.g., McBride & O'Neill, supra], capturing the VNTRs on the array, selectively dissociating the hybrid and eluting the VNTR from the support. A selected lane from the array may be cut out of the support, the ssDNA eluted therefrom, the number of copies thereof increased by PCR amplification and size analysis conducted by a conventional technique (e.g., gel electrophoresis against DNA size markers). The presence of large molecular weight strands would indicate an increase in mutational frequency (i.e., higher orders of tandem repeat regions).

The invention may be better understood with reference to the accompanying example that is intended for purposes of illustration only and should not be construed as in any sense limiting the scope of the present invention as defined in the claims appended hereto.

EXAMPLE

Oligonucleotides were synthesized directly from monomers onto a 6.6×6.6 cm sheet of aminated polypropylene substrate using standard CED-phosphoramidite chemistries. A specially designed 64 channel chemical delivery system (Southern Array Maker™, Beckman Instruments) as described in co-pending U.S. patent application Ser. No. 08/144,954 was utilized to prepare the discrete oligonucleotide sequences in parallel rows across the polypropylene substrate. Polypropylene film was surface aminated by a radiofrequency discharge into ammonia gas as described in Matson et al., supra. The plasma-aminated film was then placed in the synthesizer. Standard phosphoramidite chemistry was performed in each of the 64 channels to create 64 different oligonucleotide sequences on the film. The substrate was then cut into 0.5 cm widths perpendicular to the oligonucleotide rows to produce a panel of 64 tandem repeat sequences. For the present study 60 trinucleotide (21 mers) and 4 dinucleotide tandem (20 mers) repeat sequences were arrayed on a vertical order shown in Table 2. The arrayed trinucleotide repeat set represents all triplet frames except $(AAA)_7$ [SEQ ID NO:10], $(CCC)_7$ [SEQ ID NO:11], $(GGG)_7$ [SEQ ID NO:12], and $(TTT)_7$ [SEQ ID NO:13] in 3'→5' direction as well as minus strand orientation.

In order to confirm that all sequences were fully represented on the panel a series of complementary probes were prepared that would verify each sequence by row position on the strip. As each triplet repeat (n) of a sufficient length in fact reads the n-1 and n-2 frames as well, only 20 probe sequences were required to identify the 60 triplet repeats on the panel. For example, row 2 containing the sequence $(AAC)_7$ [SEQ ID NO:14] also represents $(ACA)_6$ [SEQ ID NO:15] and $(CAA)_6$ [SEQ ID NO:16] (sequences found at row 5 and row 17, respectively); thus, a single tandem repeat probe which has been labeled will identify the sequences at row positions 2, 5 and 17. Four additional probe sequences were required to identify the 4 doublet tandem repeats synthesized on the strip. It is also possible to combine the sequences of non-complementary probes (i.e., those that will not self-hybridize or form hairpin loops) to reduce the total number of probes necessary to read all row positions. The following $^{32}P$ 5'-end labeled probes were prepared and used to identify all row positions 1–64 (listed in Table 2) on the panel:

| | |
|---|---|
| $(TGC)_6$; | [SEQ ID NO:17] |
| $(TGG)_4(TG)_6(TTA)_4$; | [SEQ ID NO:18] |

-continued

| | |
|---|---|
| (TGG)₄(TGA)₄; | [SEQ ID NO:19] |
| (TCG)₆; | [SEQ ID NO:20] |
| (GGC)₅; | [SEQ ID NO:21] |
| (CG)₄(GAC)₄; | [SEQ ID NO:22] |
| (TCA)₄(TAA)₄(TAC)₄; | [SEQ ID NO:23] |
| (CCA)₄(CAA)₄; | [SEQ ID NO:24] |
| (TTC)₄(TC)₆(TCC)₄; and | [SEQ ID NO:25] |
| (GAA)₄(GA)₆(GGA)₄; | [SEQ ID NO:26] |
| (GCC)₄(GCA)₄ | [SEQ ID NO:27]. | also been utilized as target materials to evaluate the test strips.

STRs were identified using the GCG sequence analysis software package (Genetics Computer Group, Inc. 1991). 11,613 bp of cosmid MDY2 (GenBank accession L00727) and 61,612 bp of a contiguous sequence containing the complete 34,977 bp sequence of cosmid 22.3 were searched for STRs.

TABLE 2

Vertical array of 64 oligonucleotides consisting of 60 triplet tandem repeat sequences (21mers) and dinucleotide tandem repeat sequences (20mers) on a polypropylene substrate

| # | Oligonucteotides 3' - - - > 5' | Seq ID No. | # | Oligonucleotides 3' - - - > 5' | Seq ID No. |
|---|---|---|---|---|---|
| 1 | AC AC AC AC AC AC AC AC AC AC | 32 | 33 | GAA GAA GAA GAA GAA GAA GAA | 62 |
| 2 | AAC AAC AAC AAC AAC AAC AAC | 14 | 34 | GAC GAC GAC GAC GAC GAC GAC | 63 |
| 3 | AAG AAG AAG AAG AAG AAG AAG | 33 | 35 | GAG GAG GAG GAG GAG GAG GAG | 64 |
| 4 | AAT AAT AAT AAT AAT AAT AAT | 34 | 36 | GAT GAT GAT GAT GAT GAT GAT | 65 |
| 5 | ACA ACA ACA ACA ACA ACA ACA | 35 | 37 | GCA GCA GCA GCA GCA GCA GCA | 66 |
| 6 | ACC ACC ACC ACC ACC ACC ACC | 36 | 38 | GCC GCC GCC GCC GCC GCC GCC | 67 |
| 7 | ACG ACG ACG ACG ACG ACG ACG | 37 | 39 | GCG GCG GCG GCG GCG GCG GCG | 68 |
| 8 | ACT ACT ACT ACT ACT ACT ACT | 38 | 40 | GCT GCT GCT GCT GCT GCT GCT | 69 |
| 9 | AGA AGA AGA AGA AGA AGA AGA | 39 | 41 | GGA GGA GGA GGA GGA GGA GGA | 70 |
| 10 | AGC AGC AGC AGC AGC AGC AGC | 40 | 42 | GGC GGC GGC GGC GGC GGC GGC | 71 |
| 11 | AGG AGG AGG AGG AGG AGG AGG | 41 | 43 | AG AG AG AG AG AG AG AG AG AG | 72 |
| 12 | AGT AGT AGT AGT AGT AGT AGT | 42 | 44 | GGT GGT GGT GGT GGT GGT GGT | 73 |
| 13 | ATA ATA ATA ATA ATA ATA ATA | 43 | 45 | GTA GTA GTA GTA GTA GTA GTA | 74 |
| 14 | ATC ATC ATC ATC ATC ATC ATC | 44 | 46 | GTC GTC GTC GTC GTC GTC GTC | 75 |
| 15 | ATG ATG ATG ATG ATG ATG ATG | 45 | 47 | GTG GTG GTG GTG GTG GTG GTG | 76 |
| 16 | ATT ATT ATT ATT ATT ATT ATT | 46 | 48 | GTT GTT GTT GTT GTT GTT GTT | 77 |
| 17 | CAA CAA CAA CAA CAA CAA CAA | 47 | 49 | TAA TAA TAA TAA TAA TAA TAA | 78 |
| 18 | CAC CAC CAC CAC CAC CAC CAC | 48 | 50 | TAC TAC TAC TAC TAC TAC TAC | 79 |
| 19 | CAG CAG CAG CAG CAG CAG CAG | 28 | 51 | TAG TAG TAG TAG TAG TAG TAG | 80 |
| 20 | CAT CAT CAT CAT CAT CAT CAT | 49 | 52 | TAT TAT TAT TAT TAT TAT TAT | 81 |
| 21 | CCA CCA CCA CCA CCA CCA CCA | 50 | 53 | TCA TCA TCA TCA TCA TCA TCA | 82 |
| 22 | CG CG CG CG CG CG CG CG CG CG | 51 | 54 | TCC TCC TCC TCC TCC TCC TCC | 83 |
| 23 | CCG CCG CCG CCG CCG CCG CCG | 52 | 55 | TCG TCG TCG TCG TCG TCG TCG | 84 |
| 24 | CCT CCT CCT CCT CCT CCT CCT | 53 | 56 | TCT TCT TCT TCT TCT TCT TCT | 85 |
| 25 | CGA CGA CGA CGA CGA CGA CGA | 54 | 57 | TGA TGA TGA TGA TGA TGA TGA | 86 |
| 26 | CGC CGC CGC CGC CGC CGC CGC | 55 | 58 | TGC TGC TGC TGC TGC TGC TGC | 87 |
| 27 | CGG CGG CGG CGG CGG CGG CGG | 56 | 59 | TGG TGG TGG TGG TGG TGG TGG | 88 |
| 28 | CGT CGT CGT CGT CGT CGT CGT | 57 | 60 | TGT TGT TGT TGT TGT TGT TGT | 89 |
| 29 | CTA CTA CTA CTA CTA CTA CTA | 58 | 61 | TTA TTA TTA TTA TTA TTA TTA | 90 |
| 30 | CTC CTC CTC CTC CTC CTC CTC | 59 | 62 | TTC TTC TTC TTC TTC TTC TTC | 91 |
| 31 | CTG CTG CTG CTG CTG CTG CTG | 60 | 63 | TTG TTG TTG TTG TTG TTG TTG | 92 |
| 32 | CTT CTT CTT CTT CTT CTT CTT | 61 | 64 | CT CT CT CT CT CT CT CT CT | 93 |

A number of different test DNAs were employed. This included a 5'-(CAG)₇-3' oligonucleotide [SEQ ID NO:28] and 200 bp PCR fragments containing a trinucleotide short tandem repeat of (CTG)₁₁ [SEQ ID NO:29] [Fu, Y. H., et al, Science 255, 1256–1258 (1992)] generated from human genomic DNA of a wild type individual. An 800 bp PCR fragment containing a (CAG)₁₀ [SEQ ID NO:30] repeat and a 3.0 kb PCR fragment containing a tandemly combined (GCA)₈+(GCG)₄ repeat [SEQ ID NO:31] were generated from cDNA clones G13 and A12, respectively, recently isolated in a new cDNA identification system [Lee, C. C., et al., Am. J. Hum. Genet. 53 (Suppl.), 1321 (1993)]. DNA samples of the cosmid MDY2 [Fu, Y. H., et al, Science 255, 1256–1258 (1992)] containing the entire myotonin protein kinase gene and cosmid 22.3 containing the FMR-1 gene [Verkerk, A. J. M. H., et al., Cell 65, 905–914 (1991)] have Oligonucleotide probes were end-labelled with $^{32}$P-Gamma-dATP under standard conditions [Sambrook, J., et al., Molecular Cloning: A Laboratory Manual, Second Edition. Cold Spring Harbor Laboratory Press, Cold Spring Harbor (1989)]. Double stranded DNA was radiolabelled with $^3$P-Alpha-dCTP using a Pharmacia random priming labelling kit according to the manufacturer's instructions. To improve the labelling reaction cosmid DNA was digested with EcoRI prior to radiolabelling. The test strips were hybridized without prehybridization in plastic bags containing 6× SSCP (saline, sodium citrate-phosphate buffer) and 0.01% sodium dodecyl sulfate (SDS) for 16 hrs. Only target-specific binding to the polypropylene membranes was observed, eliminating the need for a prehybridization step. The specific activity of the radiolabelled probes was adjusted to 5×10⁶ cpm/ml hybridization solution. After hybridization the test strips were washed in 2×SSCP, 0.01%

SDS for 20 min. A variety of hybridization and wash temperatures was employed, as hereinafter described. Autoradiograms were developed after 5 minutes to 6 hours exposure at −70° C. The resulting signals on the test strips were evaluated visually.

As expected, the synthetic $(CAG)_7$ [SEQ ID NO:28] oligonucleotide probe hybridized specifically at 60° C. to three rows of the array. These corresponded to the oligonucleotide repeats $(CGT)_7$ [SEQ ID NO:57], $(GTC)_7$ [SEQ ID NO:69], and $(TCG)_7$ [SEQ ID NO:84], respectively.

Using double-stranded DNA of 200 bp and 800 bp containing a $(CTG)_{11}$ [SEQ ID NO:29] and a $(CAG)_{10}$ [SEQ ID NO:30] repeat resulted in a pattern of 6 bands corresponding to $(ACG)_7$ [SEQ ID NO:37], $(CGA)_7$ [SEQ ID NO:54], $(CGT)_7$ [SEQ ID NO:57], $(GAC)_7$ [SEQ ID NO:63], $(GTC)_7$ [SEQ ID NO:75], and $(TCG)_7$ [SEQ ID NO:84]—i.e., the sense and antisense orientations. Differences in the signal intensity were observed between the various triplet-representing lanes.

Using the 3 kb PCR fragment containing a combined repeat $(GCA)_8+(GCG)_4$ [SEQ ID NO:31] to probe the test strips resulted in a complete set of six oligonucleotides— $(ACG)_7$ [SEQ ID NO:37], $(CGA)_7$ [SEQ ID NO:54], $(CGT)_7$ [SEQ ID NO:57], $(GAC)_7$ [SEQ ID NO:63], $(GTC)_7$ [SEQ ID NO:75], and $(TCG)_7$ [SEQ ID NO:84]. This set represents the six different frame shifts for the $(GCA)_8$ [SEQ ID NO:94] repeat. Additionally, the signals found with $(CCG)_7$ [SEQ ID NO:52], $(CGC)_7$ [SEQ ID NO:55], and $(GCC)_7$ [SEQ ID NO:67]were evident for the 3'→5' directed frame of the $(GCG)_4$ [SEQ ID NO:95] repeat. No signal was detected under these conditions for the reversed direction indicated by $(GGC)_7$ [SEQ ID NO:71], $(GCG)_7$ [SEQ ID NO:68], and $(CGC)_7$ [SEQ ID NO:55].

Using cosmid MDY2 with an insert size of 31 kb as a probe, a band pattern was observed indicative of the presence of $(CAG)_n$, $(GCC)_n$, and $(CCT)_n$ repeats, respectively. For the $(CCT)_n$, only one direction of the oligonucleotide frame as represented by $(CCT)_7$ [SEQ ID NO:53], $(CTC)_7$ [SEQ ID NO:59], and $(TCC)_7$ [SEQ ID NO: 83] was found to hybridize. A search of 11,613 nt available sequence information (GenBank accession L00727) of cosmid MDY2 revealed the presence of all types of triplet repeats identified by the test strip (Table 3). The repeated triplet numbers vary from 3 for the CCT and GCG type repeats to 11 for the CTG repeat.

TABLE 3

| Position (Nucleotide #) | STR |
| --- | --- |
| 809–817 | $(CCT)_3$ |
| 8,172–8,180 | $(CCT)_3$ |
| 9,093–9,101 | $(GGA)_3$ |
| 10,364–10,372 | $(GCC)_3$ |
| 10,677–10,709 | $(CTG)_{11}$ [SEQ ID NO:29] |

Figure 2B:
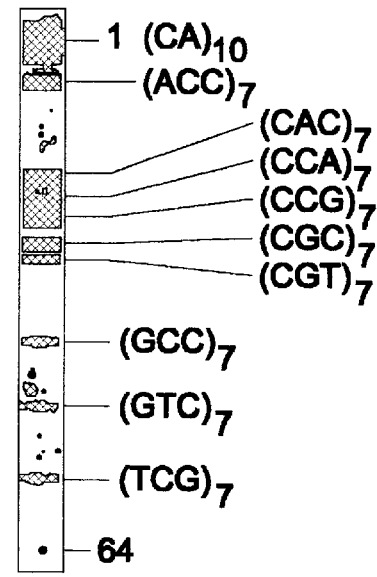
Figure 2C:
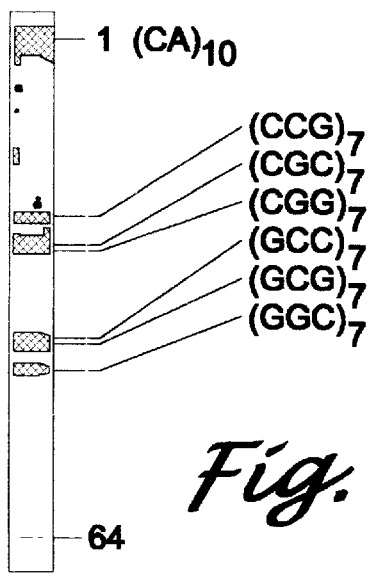

The influence of temperature on the STR detection was evaluated by hybridizing cosmid 22.3 at 40° C., 50° C., and 60° C. to the test strips. The strips were then washed at the temperatures used for the respective hybridizations. At 40° C., a band pattern was obtained indicative of $(CA)_n$, $(ACC)_n$, $(CCT)_n$ and $(GCC)_n$ type repeats, respectively (FIG. 2A); for the triplet repeats, only one set of signals representing one direction of the oligonucleotide frame was observed. The pattern at 50° C. was also specific for $(CA)_n$, $(ACC)_n$, and $(GCC)_n$ type repeats (FIG. 2B); however, unlike the pattern at 40° C. the signals representing a $(TCC)_n$ type repeat disappeared and additional bands indicative of a $(CGT)_n$ type repeat occurred; again, for the trinucleotide repeats only one set of signals representing one direction of the respective oligonucleotide frame was found. At 60° C. only signals representing $(CA)_n$ and $(CCG)_n$ type repeats persisted (FIG. 2C). Under these hybridization conditions a full set of the expected 6 bands evident for a $(CCG)_n$ type repeat was observed.

Figure 3:
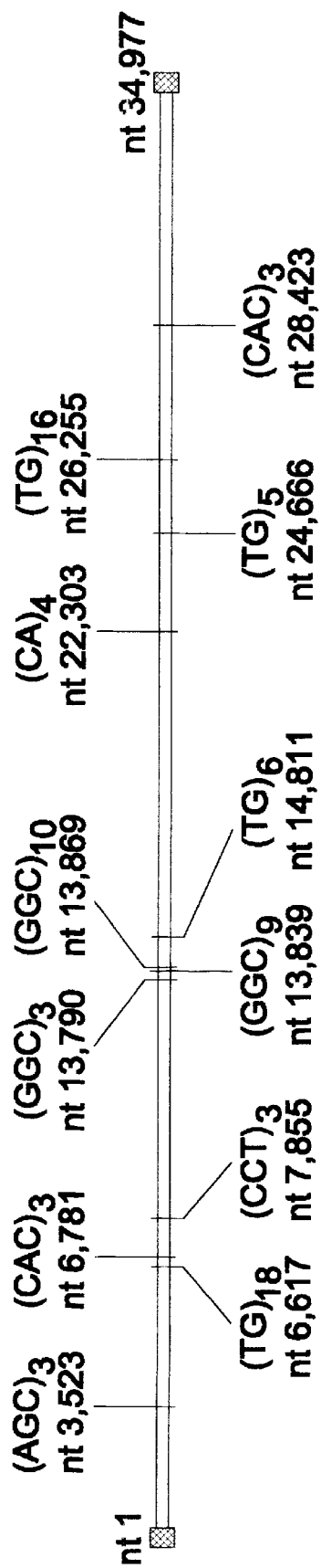
FIG. 3 illustrates the type and position of STRs indicated by the STR-Strips in 34,977 bp of cosmid 22.3.

All types of STRs indicated by the test strips were found to be present in 34,977 bp sequence available from cosmid 22.3 (FIG. 3). They range from a single repeat unit of $(CCT)_3$ and $(AGC)_3$ up to 18 repeat units for a (TG)-dinucleotide repeat. There was no unspecific hybridization signal observed. AT-rich repeats also occurring in the sequence in three or less repeat units were not detected by the test strips under the hybridization conditions used.

The array was designed to represent trinucleotide repeats by all three possible frames in 3'→5' direction, as well as in the reverse direction. Thus, using single stranded DNA a complementary sequence to a given trinucleotide repeat should result in three signals on the test strips; using double stranded DNA six respective bands for a given repeat should occur. For the four dinucleotide repeats only one frame was used for each type. Using this reverse blotting system, the obtained band pattern provided qualitatively the precise identification of previously known STRs in DNA samples of various complexities between 21 bp–34,977 bp. Moreover, there was no random or cross hybridization to unspecific sequences observed. Based on the Tm and size of the STRs as well as possible influences by flanking sequences, varying the hybridization stringency can enhance the specificity.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A method for determining size of tandem nucleotide repeats in a sample containing same, the method comprising:

bringing the sample into contact under hybridization condition with an array comprising a plurality of oligonucleotides fixedly attached to a solid support, the plurality of oligonucleotides consisting essentially of a set of tandem nucleotide repeats including sequences complementary to tandem nucleotide repeats in the sample, the array establishing a predetermined pattern, identifying the tandem nucleotide repeats in the sample by locating in the pattern the position of the complementary strand of the tandem nucleotide repeats upon hybridization of the sample to the array;

selectively dissociating the hybrids to elute the tandem nucleotide repeat from the support; and sizing the eluted tandem nucleotide repeats.

2. A method according to claim 1, wherein the eluted tandem nucleotide repeats are sized by gel electrophoresis against DNA size markers.

* * * * *